(12) United States Patent
Tan et al.

(10) Patent No.: US 7,482,149 B2
(45) Date of Patent: Jan. 27, 2009

(54) INHIBITION OF SARS CORONAVIRUS INFECTION WITH CLINICALLY APPROVED ANTIVIRAL DRUGS

(75) Inventors: Emily Li Chuan Tan, Singapore (SG); Lawrence W. Stanton, Singapore (SG)

(73) Assignee: Genome Institute of Singapore, Singapore (SG)

( * ) Notice: Subject to any disclaimer, the term of this patent is extended or adjusted under 35 U.S.C. 154(b) by 56 days.

(21) Appl. No.: 10/560,198

(22) PCT Filed: Jun. 9, 2004

(86) PCT No.: PCT/SG2004/000173

§ 371 (c)(1), (2), (4) Date: Dec. 8, 2005

(87) PCT Pub. No.: WO2004/108151

PCT Pub. Date: Dec. 16, 2004

(65) Prior Publication Data

US 2006/0153803 A1      Jul. 13, 2006

Related U.S. Application Data

(60) Provisional application No. 60/476,611, filed on Jun. 9, 2003.

(51) Int. Cl.
  C12N 7/00         (2006.01)
  C12N 7/06         (2006.01)
  A61K 38/21        (2006.01)

(52) U.S. Cl. .................. 435/235.1; 435/238; 424/85.6; 424/85.7

(58) Field of Classification Search .................. None
See application file for complete search history.

(56) References Cited

U.S. PATENT DOCUMENTS

| | | | |
|---|---|---|---|
| 4,588,585 A | 5/1986 | Mark et al. | |
| 6,350,589 B1 | 2/2002 | Morris et al. | |
| 6,685,931 B1 | 2/2004 | Grint et al. | |
| 2005/0002901 A1* | 1/2005 | Blatt | 424/85.7 |
| 2006/0280723 A1* | 12/2006 | Jervis | 424/85.6 |

OTHER PUBLICATIONS

Package insert, Betaferon® [online], Jul. 12, 1995. [retrieved on Jul. 18, 2007]. Retrieved from the Internet <URL: http://www.itri.brighton.ac.uk/projects/pills/corpus/PIL/data/Schering/Betaferon/Betaferon.html>.*

Stockman et al, Plos Medicine 3(9):e343 1525-1531, 2006.*

Tai, Annals of the Academy of Medicine Singapore, 36 (6): 438-443, 2007.*

World Health Organization. Acute respiratory syndrome in China—update 3: disease outbreak reported: Geneva: The Organization; 2003.

Lee, N., Hui, D.H., Wu, A., Chan, P., Cameron, P., Joynt, G.M., et al. A major outbreak of severe acute respiratory syndrome in Hong Kong. N Engl J Med 2003, 348:1986-94.

Ksiazek, T.G., Erdman, D., Goldsmith, C., Zaki, S.R., Peret, T., Emery, S., et al. A novel coronavirus associated with severe acute respiratory syndrome. N Engl J Med 2003, 348:1953-66.

Tsang, K.W., Ho, P.L., Ooi, G.C., Yee, W.K., Wang, T., Chan-Yeung, M., et al. A cluster of cases of severe acute respiratory syndrome in Hong Kong. N Engl J Med 2003, 348:1977-85.

Severe acute respiratory syndrome (SARS) and coronavirus testing—United States, 2003. Morb Mortal Wkly Rep 2003, 52:297-302.

Peiris, J.S.M., Chu, C.M., Cheng, V.C., Chan, K.S., Hung, I.F., Poon, L.L., et al. Clinical progression and viral load in a community outbreak of coro-navirus-associated SARS penumonia: a prospective study. Lancet 2003, 361:1767-72.

Chan-Yeung, M., Yu, W.C. Outbreak of severe acute respiratory syndrome in Hong Kong Special Administrative Region: case report. BMJ 2003, 326:850-2.

Nicholls, J.M., Poon, L.L., Lee, K.C., Ng, W.F., Lai, S.T., Leung, C.Y., et al. Lung pathology of fatal severe acute respiratory syndrome. Lancet 2003, 361:1773-8.

Poutanen, S.M., Low, D.E., Henry, B., Finkelstein, S., Rose, D., Green, K., et al. Identification of severe acute respiratory syndrome in Canada. N Engl J Med 2003, 348:1995-2005.

Drosten, C., Gunther, S., Preiser, W., Van Der Werf, S., Brodt, H.R., Becker, S., et al. Identification of a novel coronavirus in patients with severe acute syndrome. N Engl J Med 2003, 348:1967-76.

Lapinsky, S.E. and Hawryluck, L. ICU management of severe acute respiratory syndrome. Intensive Care Med 2003, 29:870-5.

Booth, C.M., Matukas, L.M., Tomlinson, G.A., Rachlis, A.R., Rose, D.B., Dwosh, H.A., et al. Clinical features and short-term outcomes of 144 patients with SARS in the greater Toronto area. JAMA 2003, 289:2801-9. Erratum in: JAMA 2003, 290:334.

Driscoll, J.S. Antiviral drugs. Aldershot, UK: Ashgate Publishing Ltd, 2002.

Ruan, Y.J., Wei, C.L., EE, A.L., Vega, V.B., Thoreau, H., Su, S.T., et al. Comparative full length genome sequence analysis of 14 SARS coro-navirus isolates and common mutations associated with putative origins of infection. Lancet 2003, 361:1779-85. Erratum in: Lancet 2003, 361:1832.

Richmond, J.Y. and McKinney, R.W. Biosafety in microbiological and biomedical laboratories. 4th ed. Washington: U.S. Government Printing Office, 1999.

Al-Jabri, A.A., Wigg, M.D. and Oxford, J.S. Initial in vitro screening of drug candidates for their potential antiviral activities. In: Mahy, B.W.J. and Kangro H.O. eds. Virology Methods Manual. Academic Press Ltd. London. 1996: 293-356.

Huffman, J.H., Sidwell, R.W., Khare, G.P., et al. In vitro effect of 1-beta-D- ribofuranosyl-1,2,4-triazole-3-carboxamide (Virazole, ICN-1229) on deoxy-ribonucleic acid and ribonucleic acid viruses. Antimicrob Agents Chemo. 1973, 3:235-241.

(Continued)

*Primary Examiner*—Mary E Mosher
(74) *Attorney, Agent, or Firm*—Klarquist Sparkman, LLP (57) ABSTRACT

The invention relates to methods for treating or inhibiting SARS-CoV infection involving the administration of an interferon, particularly IFN α-n1, IFN α-n3, human leukocyte IFN α or IFN β-1b.

8 Claims, 2 Drawing Sheets

OTHER PUBLICATIONS

Saganuma, T. and Ishida, N. An evaluation of a new antiviral agent 'Virazole' against influenza virus infections. Tohoku J. Exp. Med. 1973, 110: 405-406.

Morrey, J.D., Smee, D.F., Sidwell, R.W., and Tseng, C. Identification of active antiviral compounds against a New York isolate of West Nile virus. Antiviral Res 2002. 55:107-16.

Davis, G.L., et al. Interferon alpha2b alone or in combination with Ribavirinfor the treatment of relapse of chronic hepatitis. N. Engl. J. Med. 1998, 339:1493-1499.

Poynard, T.P., et al. Randomised trial for interferon alpha2b plus Ribavirin. Lancet 1998, 352;1426-1432.

McHutchison, J.G., et al. Interferon alpha2b alone or in combination with Ribavirin as initial treatment for hepatitis C. N. Engl. J. Med. 1998, 339:1485-1492.

Pfeffer, L.M., et al. Biological properties of recombinant alpha-interferons: 40th anniversary of the discovery of interferons. Cancer Res. 1998, 58:2489-2499.

Lee, C.K., Bluyssen, H.A. and Levy, D.E., Regulation of interferon alpha responsiveness by the duration of Janus kinase activity J. Biol. Chem. 1997, 272:21872-21877.

Turner, R.B., Felton, A., Kosak, K., Kelsey, D.K., and Meschievitz, C.K. Prevention of experimental coronavirus colds with intranasal alpha-2b interferon. J Infect Dis 1986; 154:443-7.

Higgins, P.G., Phillpotts, R.J., Scott, G.M., Wallace, J., Bernhardt, L.L., and Tyrrell, D.A. Intranasal interferon as protection against experimental respiratory coronavirus infection in volunteers. Antimicrob Agents Chemother 1983: 24:713-5.

Tyrell, D.A. The efficacy and tolerance of intranasal interferons: studies at the common cold unit. J Antimicrob Chemother 1986; 18B:153-6.

Weingartl, H.M., and Derbyshire, J.B. Antiviral activity against transmissible gastroenteritis virus, and cytotoxicity, of natural porcine interferons alpha and beta. Can J Vet Res 1991; 55:143-9.

Jordan, L.T., and Derbyshire, J.B. Antiviral activity of interferon against transmissable gastroenteritis virus in cell culture and ligand intestinal segments in neonatal pigs. Vet Microbiol 1994; 38:263-76.

Tan, Emily L.C., et al. Inhibition of SARS Coronavirus Infection In Vitro with Clinically Approved Antiviral Drugs. Emerging Infections Deseases. Apr. 2004. vol. 10, No. 4. pp. 581-586.

Cinatl, J. et al., Treatment of SARS with Human Interferons, The Lancet, Jul. 26, 2003, pp. 293-294, vol. 362, Issue 9380.

Healthopedia.com Drugs Information, Interferons, Alpha (Systemic), Date revised Sep. 12, 2001, Retrieved on Oct. 4, 2007 from the Internet: URL:http://www.healthopedia.com/drugs/detailed/interferons-alpha.

* cited by examiner

大專用語ーー]
INHIBITION OF SARS CORONAVIRUS INFECTION WITH CLINICALLY APPROVED ANTIVIRAL DRUGS

CROSS REFERENCE TO RELATED APPLICATION

This application claims the benefit of U.S. Provisional Application Ser. No. 60/476,611, filed Jun. 9, 2003, which is herein incorporated by reference.

FIELD OF THE INVENTION

The present invention relates generally to treatment of viral infection, and particularly to SARS-CoV infection.

BACKGROUND OF THE INVENTION

Severe acute respiratory syndrome (SARS) (1,2) is an infectious disease caused by a newly identified human coronavirus (SARS-CoV) (3,4). SARS-CoV has a single-stranded, positive-sense RNA genome of 30 kb, and encodes 14 potential open reading frames (ORFs).

Symptoms of SARS includes fever over 38° C. and other symptoms such as headache, an overall feeling of discomfort, body aches and mild respiratory symptoms at the outset. About 10 percent to 20 percent of patients have diarrhea After 2 to 7 days, SARS patients may develop a dry cough. Most patients develop pneumonia SARS is a highly contagious infectious disease and has a mortality rate of 15 to 20%. Currently, no effective drug exists to treat SARS-CoV infection (5).

Intensive efforts are under way to gain more insight into the mechanisms of SARS-CoV replication, in order to develop targeted antiviral therapies and vaccines. Developing effective and safe vaccines and chemotherapeutic agents against SARS-CoV, however, may take years. The recent epidemic has shown that knowledge is lacking regarding the clinical management and treatment of infected patients. Ribavirin (6-12), oseltamivir (8-10), foscarnet (8), intravenous immunoglobulin (8), and other agents have been used to treat patients. Preliminary results from in vitro testing indicate that ribavirin concentrations that inhibit other viruses sensitive to ribavirin do not inhibit replication or cell-to-cell spread of the SARS-CoV (5). However, the U.S. Centers for Disease Control and Prevention concluded that further in vitro testing of antiviral drugs on other coronavirus isolates and more information on the clinical outcome of patients treated with ribavirin or other antiviral drugs in controlled trials is needed (5).

SUMMARY OF THE INVENTION

The present invention relates to methods and uses of various interferons to inhibit SARS-CoV infection. Thus, in one aspect, the present invention provides a method of treating SARS-coronavirus infection, comprising administering an effective amount of an interferon to a patient, wherein the interferon is IFN α-n1, IFN α-n3, human leukocyte IFN α or IFN β-1b. The invention also provides use of an effective amount of an interferon for treating SARS-coronavirus infection, and use of an effective amount of an interferon in the manufacture of a medicament for treating SARS-coronavirus infection, wherein the interferon is IFN α-n1, IFN α-n3, human leukocyte IFN α or IFN β-1b.

In another aspect, the invention provides a method of inhibiting SARS-coronavirus infection, the method comprising administering an interferon to a cell capable of being infected with SARS-CoV, wherein the interferon is IFN α-n1, IFN α-n3, human leukocyte IFN α or IFN β-1b. The invention also provides use of an interferon for inhibiting SARS-coronavirus infection, and use of an interferon in the manufacture of a medicament for inhibiting SARS-coronavirus infection, wherein the interferon is IFN α-n1, IFN α-n3, human leukocyte IFN α or IFN β-1b.

The present invention also provides kits for use in practicing the methods of the invention. In various aspects, there is provided a kit comprising an interferon and instructions for using the interferon to treat SARS-coronavirus infection, or to inhibit SARS-coronavirus, wherein the interferon is IFN α-n1, IFN α-n3, human leukocyte IFN α or IFN β-1b.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION OF EMBEDMENTS

The present invention relates to the discovery that certain interferon (IFN) subtypes inhibit infection by SARS coronavirus (SARS Co-V).

Interferons are a class of proteins produced by a host organism to combat viral infection and tumour development. Host cells, when infected by a virus, synthesize and secrete interferon, which then binds to receptors on healthy cells and induces an antiviral response mechanism in such cells. The biologic response properties of interferons are mediated through its interactions with specific surface cell receptors, leading to activation of the JAK/STAT pathway and production interferon-stimulated gene products such as 2'5'-oligoadenylate synthase and protein kinase PKR (24). The antiviral activity of interferons is mediated by direct effects on infected cells or through an induced immune response (23).

The inventors have discovered that certain interferon subtypes, particularly IFN α-n1, IFN α-n3, human leukocyte IFN α and IFN β-1b, inhibit SARS-CoV infection in Vero E6 cells in vitro. The results indicate that various IFNs can be used to inhibit SARS-CoV infection, and therefore are useful in the treatment of individuals infected with SARS-CoV.

The invention therefore provides a method of treating SARS-CoV infection by administering an effective amount of an interferon to a patient. The invention also provides a method of inhibiting SARS-CoV infection, comprising administering an interferon to a cell capable of being infected with SARS-CoV.

"Treating" SARS-CoV infection refers to an approach for obtaining beneficial or desired results, including, but not limited to, eradication, alleviation or amelioration of infection, diminishment of extent of infection and prevention or slowing of progression or spread of infection. As will be understood by a skilled person, results may not be beneficial or desirable if, while improving a state of infection in a patient, the treatment results in adverse effects on the patient treated which outweigh any benefits effected by the treatment.

The interferon is an interferon that is capable of inhibiting SARS-CoV infection. Inhibiting SARS-CoV or inhibiting SARS-CoV infection refers to the ability of a particular interferon to prevent or reduce invasion by SARS-CoV into cells to thereby cause SARS, either in a patient or in vitro, or to prevent or reduce SARS-CoV from spreading from infected cells to uninfected cells to thereby prolong an existing infection, either within an infected individual or in vitro, or to prevent SARS-CoV from replicating within an infected cell. The interferon as that term is used herein includes a full-length interferon and a fragment of a full-length interferon that maintains the inhibitory activity of the full-length interferon. A skilled person will be able to determine whether a fragment of a full-length interferon is capable of maintaining the inhibitory activity, including an antiviral response, in a target cell, for example as described in the Examples.

The interferon may be an interferon isolated and purified from a cell population that normally produces interferon, for example leukocytes or lymphoblastoid cells. Alternatively, the interferon may be a recombinant interferon, produced by the cloning and expression of an interferon gene in an expression system, for example, recombinantly produced in $E.$ $coli$ or mammalian cell culture, and subsequent purification of the expressed interferon. Recombinant protein expression techniques are known in the art, and described for example in Sambrook et al. ((2001) Molecular Cloning: a Laboratory Manual, $3^{rd}$ ed., Cold Spring Harbour Laboratory Press). Interferons that are approved for clinical use are commercially available, including recombinant interferons and interferons isolated from a natural source. Such commercially available interferons include Roferon™ (Roche), Intron A™ (Schering-Plough), Wellferon™ (Glazosmithkline), Alferon™ (Hemispheryx), Rebif™ (Serono), Betaferon™ (Schering AG) and Multiferon™ (Viragen International Inc).

In certain embodiments, the interferon is IFN α-n1, IFN α-n3, human leukocyte IFN α or IFN β-1b.

The cell may be one or more cells capable of being infected with SARS-CoV, meaning SARS-CoV is able to infect such cells, and includes a cell that is already infected with SARS-CoV. Such a cell or cells May be in a patient, or may be a cell in vitro, for example, an isolated cell, or a cell that is part of a cell population or cell culture. Cells that are capable of being infected by SARS-CoV include epithelial cells, blood cells, including macrophages, and cells of heart, liver, kidneys, or eyes. Identification of cells that are capable of being infected with SARS-CoV may be achieved by growing cells in vitro, and performing a standard plaque assay using SARS-CoV. Alteratively, cell samples may be taken from an individual known to be, or suspected of being, infected with SARS-CoV, and tested for the presence of SARS-CoV, for example by using PCR amplification methods to detect the presence of the viral genome in particular cell types isolated from the patient.

The cell may be a human cell, for example, peripheral blood leukocytes or a THP-1 monocytic cell, or it may be derived from another species, where that cell is capable of being infected by SARS-CoV, for example a VERO 6 cell.

When the cell is an in vitro cell, administering may be achieved by adding the interferon to the growth medium, either prior to exposure of the cells to SARS-CoV so as to prevent infection of the cells by the virus, or after to exposure to SARS-CoV, or concomitantly with SARS-CoV.

The patient may be any animal, including a human. In a particular embodiment, the patient is a human.

The interferon may be administered to a patient using standard methods of administration. In various embodiments, the interferon is administered systemically, including orally, parenterally or by any standard method known in the art.

When administered to a patient, an effective amount of the interferon is the amount required, at the dosages and for sufficient time period, to ameliorate, to alleviate, improve, mitigate, ameliorate, stabilize, prevent the spread of, slow or delay the progression of or cure the infection. For example, it may be an amount sufficient to achieve the effect of reducing or eliminating viral load, or the effect of reducing or stabilizing the number of cells infected with SARS-CoV, or inhibiting the replication and/or proliferation of SARS-CoV, or preventing or slowing the spread of virus from infected to uninfected cells.

The effective amount to be administered to a patient can vary depending on many factors such as the pharmacodynamic properties of the interferon, the mode of administration, the age, health and weight of the patient, the nature and extent of the disease state, the frequency of the treatment and the type of concurrent treatment, if any, and the protein activity of the interferon preparation.

One of skill in the art can determine the appropriate amount based on the above factors. The interferon may be administered initially in a suitable amount that may be adjusted as required, depending on the clinical response of the patient. The effective amount of interferon can be determined empirically and depend on the maximal amount of the interferon that can be administered safely, and the minimal amount of the interferon that produces the desired result.

The concentration of interferon to be administered will vary depending on the ability of the particular type or subtype of interferon that is to be administered, as well as the source of interferon and amount of glycosylation. For example, for certain subtypes of IFN α, the amount may vary from about 3-5 million IU three times a week to about 5 million IU daily for administration into a human patient. For IFN β subtypes, doses of about 3-6 million IU may be administered three times weekly. Plasma levels of interferons administered via the subcutaneous route are usually low with correspondingly short half-lives. In view of their mechanism of action, absolute serum levels may not be meaningful as a measure of the biological activity of interferons, compared to induction of cellular products such as 2'5'-oligoadenylate synthase.

Effective amounts of interferon can be given repeatedly, depending upon the effect of the initial treatment regimen. Administrations are typically given periodically, while monitoring any response. It will be recognized by a skilled person that lower or higher dosages than those indicated above may be given, according to the administration schedules and routes selected.

The interferon may be administered alone or in combination with an additional antiviral agent. The additional antiviral agent may be any agent that exhibits an antiviral effect when administered to an individual infected with SARS-CoV. For example the other antiviral agent may be a nucleoside analogue, a protease inhibitor, a reverse transcriptase inhibitor, a neuraminidase inhibitor, or a receptor antagonist.

For example, in one embodiment, tie interferon is administered in combination with ribavirin. Ribavirin is a nucleoside analogue, and as set out in the Examples below, inhibitory activity was observed at all viral loads tested, albeit with relatively high concentrations of ribavirin (0.5 to 5 mg/mL).

However, concentrations of ribavirin required to demonstrate an inhibitory effect on SARS-CoV resulted in observed slight cytotoxicity. These results indicate that although ribavirin is not suitable for treatment of SARS-CoV infection alone, it may be used in combination with other treatments at lower doses. Thus, in certain embodiments, ribavirin may be administered in combination with the interferon. In some embodiments, the dose of ribavirin administered to a human subject in combination with the interferon is between about 600 and about 1200 mg per day, which dose has been shown to be effective as a combination therapy against hepatitis C infection, see for example U.S. Pat. No. 6,685,931, which is herein incorporated by reference.

In combination with refers to concurrent or sequential administration of interferon and an additional antiviral agent. When administered concurrently, the interferon and additional antiviral agent may be administered together, in the same vehicle or dosage form, or may be administered in separate vehicles or dosage forms, although administered at the same time. When administered sequentially, the administration of the interferon, if given in multiple doses, may overlap with the timing of the administration of one or more dose of the additional antiviral agent, such that the two are administered within the course of a common treatment schedule to achieve the desired combined treatment effect. The routes of administration of the interferon and the additional antiviral agent, whether administered concurrently in different vehicles or dosage forms, or administered sequentially, may be the same or different.

The interferon may be administered alone or in combination with a pharmaceutically acceptable carrier, the proportion of which is determined by the solubility and chemical nature of the interferon, chosen route of administration and standard pharmaceutical practice.

To ease administration, the interferon may be formulated as an ingredient in a pharmaceutical composition. Therefore, in one embodiment, there is provided a pharmaceutical composition comprising an interferon and a pharmaceutically acceptable carrier, in a biologically compatible form suitable for administration in vivo.

The pharmaceutical composition may further comprise an additional viral agent, as described above, including ribavirin.

The pharmaceutical compositions may routinely contain pharmaceutically acceptable concentrations of salt, buffering agents, preservatives and various compatible carriers. For all forms of delivery, the recombinant virus may be formulated in a physiological salt solution.

The proportion and identity of the pharmaceutically acceptable carrier is determined by chosen route of administration, compatibility with an active protein and standard pharmaceutical practice. Generally, the pharmaceutical composition will be formulated with components that will not significantly impair the biological activity of the interferon.

The pharmaceutical composition can be prepared by known methods for the preparation of pharmaceutically acceptable compositions suitable for administration to patients, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the interferon in association with one or more pharmaceutically acceptable vehicles or carriers, and contained in buffer solutions having a suitable pH and which are iso-osmotic with physiological fluids.

The pharmaceutical composition may be administered to a patient in a variety of forms depending on the selected route of administration, as will be understood by those skilled in the art. The composition of the invention may be administered orally or parenterally. Parenteral administration includes intravenous, intraperitoneal, subcutaneous, intramuscular, transepithelial, transdermal, nasal, intrapulmonary, intrathecal, rectal and topical modes of administration. Parenteral administration may be by continuous infusion over a selected period of time.

The pharmaceutical composition may be administered orally, for example, with an inert diluent or with an assimilable carrier, or it may be enclosed in hard or soft shell gelatin capsules, or it may be compressed into tablets or it may be incorporated directly with the food of the diet. For oral therapeutic administration, the interferon may be incorporated with an excipient and be used in the form of ingestible tablets, buccal tablets, troches, capsules, elixirs, suspensions, syrups, wafers and the like.

The pharmaceutical compositions may also be administered parenterally or intraperitoneally. Solutions of the interferon may be prepared in a physiologically suitable buffer. Under ordinary conditions of storage and use, these preparations contain a preservative to prevent the growth of microorganisms, but that will not inactivate the interferon protein. A person skilled in the art would know how to prepare suitable formulations. Conventional procedures and ingredients for the selection and preparation of suitable formulations are described, for example, in Remington's Pharmaceutical Sciences and in The United States Pharmacopeia: The National Formulary (USP 24 NF19) published in 1999.

The forms of the pharmaceutical composition suitable for injectable use include sterile aqueous solutions or dispersion and sterile powders for the extemporaneous preparation of sterile injectable solutions or dispersions. In all cases the form must be sterile and must be fluid to the extent that easy syringability exists.

The dose of the pharmaceutical composition that is to be used depends on the severity and stage of the infection, the individual patient parameters including age, physical condition, size and weight, the duration of the treatment, the nature of concurrent antiviral therapy (if any), the specific/route of administration and other similar factors that are within the knowledge and expertise of the health practioner. These factors are known to those of skill in the art and can be addressed with minimal routine experimentation.

The interferon, or pharmaceutical compositions comprising the interferon, may be packaged as a kit and the invention in one aspect provides a kit comprising an interferon, and instructions for use of the interferon to treat SARS-CoV infection, or instructions for use of the interferon to inhibit SARS-CoV. In one embodiment, the kit may further comprise an additional antiviral agent, for example ribavirin, and instructions for concurrent or sequential administration of the interferon and additional antiviral agent, The present invention also contemplates various uses of an interferon, including the use of an interferon for treating SARS-CoV infection, use of an interferon in the manufacture of a medicament for treating SARS-CoV infection, use of an interferon for inhibiting SARS-CoV infection, and use of an interferon in the manufacture of a medicament for inhibiting SARS-CoV infection.

All references referred to herein are incorporated by reference.

EXAMPLES

The aim of this study was to investigate whether a panel of currently available antiviral agents exhibit in vitro anti-SARS-CoV activity. A cell-based assay utilizing cytopathic endpoints (CPE) was set up using Vero E6 cells to screen these antiviral compounds. SARS-CoV has been shown to infect Vero E6 cells, an African green monkey kidney cell line (3). It is also contemplated that the following method can be used in conjunction with peripheral blood leukocytes and THP-1 monocytic cell line. The initial screen was followed by a plaque reduction assay to determine the 50% effective concentration ($EC_{50}$) of compounds showing positive results. These experiments allow rapid screening of commercially available antiviral agents, enabling those with in vitro evidence of activity to move expeditiously into clinical studies, since safety and pharmacokinetic information in humans is already available for other disease indications. A total of 19 drugs approved for clinical use in the treatment of viral infections were tested, which are representative compounds from major antiviral pharmacologic classes that are currently commercially available: nucleoside analogues, interferons, protease inhibitors, reverse transcriptase inhibitors and neuraminidase inhibitors.

Materials and Methods

Selection and Preparation of Drugs: To rapidly identify a pharmacologic agent that could be used to treat SARS, a collection of antiviral drugs was tested against SARS-CoV, the etiologic agent of the atypical pneumonia To investigate a wide spectrum of potential molecular targets, we decided to cover the entire pharmacologic range of commercially available antiviral agents, including agents not expected to be active against coronaviruses. Information on antiviral drugs provided here was obtained from prescribing information sheets or from communications with the manufacturer.

Nucleoside analogues are a diverse class of compounds; in general, they inhibit viral RNA or DNA polymerases or other enzymes, interfering with nucleic acid synthesis. In this study, the selected compounds that target DNA viruses such as herpes simplex virus (HSV) and varicell-zoster viruses (VZV) were acyclovir, ganciclovir, and foscarnet. Ribavirin has activity against a range of DNA and RNA viruses; in different cell lines, $ED_{50}$ ranges from 1 to 100 μg/mL. Anti-retroviral (HIV) drugs include reverse transcriptase (RT) inhibitors and protease inhibitors. Selected HV nucleoside RT inhibitors studied were zidovudine and lamivudine, while HIV protease inhibitors studied were indinavir, nelfinavir, and saquinavir. The third group of antivirals studied were the neuraminidase inhibitors; both commercially available preparations, zanamivir and oseltamivir, were used in this study. Interferons were the next major class of antivirals studied. Various subtypes of interferon α (2a, 2b, n1, and n3, human leukocyte) and β (1a and 1b) were used. Amantadine, an old antiviral compound, was also studied. Different terms have been used to express antiviral activity, namely, 50% effective concentration ($EC_{50}$), 95% effective concentration ($EC_{95}$), 50% effective dose ($ED_{50}$), 50% inhibitory concentration ($IC_{50}$) 95% inhibitory concentration ($IC_{95}$), and minimum inhibitory concentration (MIC). Table 1 illustrates the range of activity for particular antiviral drugs against certain viruses.

TABLE 1

Inhibitory Concentrations of Antiviral Drugs against Select Viruses

| Compound | $IC_{50}$ | Virus |
|---|---|---|
| Foscavir | 50-800 μmol/L | Cytomegalovirus |
|  | 5-443 μmol/L | Herpes simplex mutants |
| Acyclovir | 0.01-13.5 μg/mL | Herpes simplex virus and varicella-zoster virus |
| Cymevene | 0.02-3.48 μg/mL | Laboratory strains or clinical isolates of cytomegalovirus |
| Ribavirin | 1-25 μg/mL | Influenza |
|  | 25-100 μg/mL | HIV and other retroviruses |
|  | 3.2-50 μg/mL (MIC) | Herpes and poxviruses suppression |
| Lamivudine | 0.0006-0.034 μg/mL | HIV |
| Zidovudine | 0.003-0.013 μg/mL | HIV |
| Fortovase | 1-30 nmol/L | HIV |
| Viracept | 7-196 nM ($EC_{95}$) | HIV |
| Crixivan | 25-100 nmol/L | HIV |
| Relenza | 0.005-16 μmol | Influenza virus |
| Tamiflu | 0.0008 μM→35 μmol | Influenza virus |
| Amantadine | 0.1-25 ($ED_{50}$) | Influenza virus |

[a]$IC_{50}$, 50% inhibitory concentration;
$EC_{95}$, 95% effective concentration;
$ED_{50}$, 50% effective dose.

Tenfold dilutions of the drug were tested to cover a broad range of concentrations above and below inhibitory dosages as reported by the manufacturer for other viral-host combinations. Compounds already present in aqueous injections were made up to volume by using Hank's buffered saline solution. For tablet and capsule formulations with soluble active ingredients, the outer coat was removed wherever applicable, and the preparation was ground in a mortar and pestle. The contents were dissolved in water, vortexed, and centrifuged thereafter at 3,000 g. The required volume was pipetted from the supernatant and diluted accordingly. When the active ingredients were insoluble in water (nelfinavir and saquinavir), the contents were dissolved in dimethylsulphoxide (DMSO); care was taken to ensure that the final concentration of DMSO in the dilutions would not exceed 1%. For plaque assays, fivefold drug dilutions were prepared by using growth media as specified below.

SARS-CoV Production and Infection: Vero E6 cells (American Type Culture Collection, Manassas, Va.) were propagated in 75 cm 2 cell culture flasks in growth medium consisting of medium 199 (Sigma, St Louis, Mo.) supplemented with 10% fetal calf serum (FCS; Biological Industries, Kibbutz Beit Haemek, Israel). SARS-CoV 2003VA2774 (an isolate from a SARS patient in Singapore), which has been previously sequenced (14), was propagated in Vero E6 cells. Briefly, 2 mL of stock virus was added to a confluent monolayer of Vero E6 cells and incubated at 37° C. in 5% $CO_2$ for 1 h; 13 mL of medium 199 supplemented with 5% FCS was then added. The cultures were incubated at 37° C. in 5% $CO_2$, and the supernatant was harvested after 48 h; in >75% of cultures, inhibition of CPE (3+) in each well was observed with an inverted microscope. The supernatant was clarified at 2,500 rpm and then divided into aliquots, placed in cryovials, and stored at −80° C. until use.

Virus Handling and Titration: All virus culture and assays were carried out in the biosafety Level 3 laboratory at the Environmental Health Institute, according to the conditions set out in Biosafety in Microbiological and Biomedical Laboratories (15). Virus titer in the frozen culture supernatant was determined by using a plaque assay. Briefly, 100 μL of virus in 10-fold serial dilution was added, in duplicates, to a monolayer of Vero E6 cells in a 24-well plate. After 1 h of incubation at 37° C. in 5% $CO_2$, the viral inoculum was aspirated, and 1 mL of carboxymethylcellulose overlay with medium 199, supplemented with 5% FCS, was added to each well. After 4 days of incubation, the cells were fixed with 10% formalin and stained with 2% crystal violet. The plaques were counted visually, and the virus titer in plaque-forming units per mL (PFU/mL) was calculated.

Cytopathic Endpoint Assay: The protocol used was adapted from Al-Jabri et al. (16), and all drugs were tested in quadruplicate. Briefly, 100 μL of serial 10-fold dilutions of the drugs were incubated with 100 μL of Vero E6 cells, giving a final cell count of 20,000 cells per well in a 96-well plate. The incubation period was 1 h at 37° C. in 5% $CO_2$, except for the interferons, which were incubated overnight with the cells. Ten microlitres of virus at a concentration of 10,000 PFU/well was then added to each of the test wells. The plates were incubated at 37° C. in 5% $CO_2$ for 3 days and observed daily for CPE. The end point was the drug dilution that inhibited 100% of the CPE ($CIA_{100}$) in quadruplicate wells. To determine cytotoxicity, 100 μL of serial 10-fold dilutions of the drugs was incubated with 100 μL of Vero E6 cells, giving a final cell count of 20,000 cells per well in a 96-well plate, without viral challenge. The plates were then incubated at 37° C. in 5% $CO_2$ for 3 days and examined for toxicity effects by using an inverted microscope.

Plaque Reduction Assay: Trypsinized Vero E6 cells were resuspended in growth medium and preincubated with interferons (serial fivefold dilution) in quadruplicate wells in 24-well plates. The next day, the medium was aspirated, and 100 μL of virus was added to each well at a titer of 100 PFU/well. After incubation for 1 h, the virus inoculum was aspirated, and a carboxymethylcellulose overlay containing maintenance medium and the appropriate interferon concentration was added. After 4 days' incubation, the plates were fixed and stained as described previously. The number of plaques was then counted visually, and the concentration of drug that inhibits 50% of plaques in each well ($IC_{50}$) was determined. Results were plotted in Microsoft Excel, and a polynomial of order three was used to approximate the data and extrapolate $IC_{50}$ and $IC_{95}$ values.

Results

Cell-based Assay of SARS-CoV Infection: High titers of infectious SARS-CoV, originally derived from a respiratory sample of a SARS patient, were propagated on Vero E6 cells. The CPE of SARS-CoV on Vero E6 was evident within 24 hours after infection (FIG. 1). SARS-CoV-infected cells display a CPE characterized by the appearance of rounded cells and the destruction of the monolayer.

Antiviral Drug Activity: A collection of 19 antiviral drugs was tested in the SARS-CoV CPE inhibition assay (Table 2). The set of drugs tested included seven interferons, five nucleoside analogues, three protease inhibitors, two RT inhibitors, and two neuraminidase inhibitors.

TABLE 2

Various Antiviral Drugs Tested for Inhibitory Effect on SARS-CoV

| Antiviral Drug | Source | Highest Concentration Tested | Inhibition of Cytopathic Effect |
|---|---|---|---|
| Interferons | | | |
| Interferon α2a (Roferon ™) | Roche | 100,000 IU/mL | No |

TABLE 2-continued

Various Antiviral Drugs Tested for Inhibitory Effect on SARS-CoV

| Antiviral Drug | Source | Highest Concentration Tested | Inhibition of Cytopathic Effect |
|---|---|---|---|
| Interferon α2b (Intron A ™) | Schering Plough | 500,000 IU/mL | No |
| Interferon αn1 (Wellferon ™) | Glaxosmithkline | 500,000 IU/mL | Yes |
| Interferon αn3 (Alferon ™) | Hemispheryx | 10,000 IU/mL | Yes |
| Interferon β1a (Rebif ™) | Serono | 500,000 IU/mL | No |
| Interferon β1b (Betaferon ™) | Schering AG | 100,000 IU/mL | Yes |
| Human Leukocyte Interferon α (Multiferon ™) | Viragen International Inc | 500,000 IU/mL | Yes |
| Nucleoside Analogues | | | |
| Acyclovir | Faulding | 1,000 μg/mL | No |
| Cymevene (Ganciclovir ™) | Roche | 50,000 μg/mL | No |
| Ribavirin | ICN Pharma | 10,000 μg/mL | Yes |
| Foscarnet (Foscavir ™) | Astrazeneca | 8,000 μmol/L | No |
| Protease Inhibitors | | | |
| Indinavir (Crixivan ™) | Merck | 100 μmol/L | No |
| Nelfinavir (Viracept ™) | Roche | 10,000 nmol/L | No |
| Saquinavir (Fortovase ™) | Roche | 10,000 nmol/L | No |
| Reverse Transcriptase Inhibitors | | | |
| Lamivudine (Epivir ™) | Glaxosmithkline | 1,000 μmol/L | No |
| Zidovudine (Retrovir ™) | Glaxosmithkline | 1,000 μg/mL | No |
| Neuraminidase Inhibitors | | | |
| Oseltamivir (Tamiflu ™) | Roche | 10,000 μmol/L | No |
| Zanamivir (Relenza ™) | Glaxosmithkline | 1,000 μmol/L | No |
| Ion Channel Blockers | | | |
| Amantadine (Symmetrel ™) | Novartis | 1,000 μg/mL | No |

Complete inhibition of the CPE was observed for four of the seven interferons in the initial screen when very high viral challenge of 10 4 PFU/well and a high multiplicity of infection (MOI=0.5) rate were used. Complete inhibition, expressed as $CIA_{100}$, was observed for interferon β-1b (Betaferon) at 5,000 IU/mL, interferon α-n3 (Alferon) at 5,000 IU/mL, interferon α-n1 (Wellferon) at 250,000 IU/mL, and human leukocyte interferon α (Multiferon) at 500,000 IU/mL. Ribavirin also completely inhibited the CPE at 5,000 μg/mL (Table 3). None of the other drugs showed complete inhibition of CPE, even at the highest concentration of drug tested (Table 2). Rebif (IFN-β-1a) showed slight inhibition of CPE at 250,000 IU/mL, but the inhibition was not complete at the screening virus load of 10,000 PFU/well. Likewise, Roferon (IFN-α-2a) showed slight, incomplete inhibition at 50,000 IU/mL.

Since the criteria for ascertaining anti-SARS-CoV activity in this screen were set at 100% inhibition of CPE, and as high doses of interferons may result in severe clinical side effects, we chose to conduct further evaluations only in the interferons that showed complete inhibition from initial screen, namely, Wellferon, Multiferon, Betaferon, and Alferon. Based upon results of the primary screen, the four active interferons and ribavirin were retested at two lower viral challenges, $10^3$ and $10^2$ PFU/well. All four drugs again showed inhibitory effect, although the $CIA_{100}$ were dependent on viral loads (Table 3). At the lowest viral loan the $CIA_{100}$ were 5 IU/mL for both interferon β-1b (Betaferon) and human leukocyte interferon α (Multiferon); and 50 and 250 IU/mL for interferon α-n3 (Alferon) and interferon α-n1 (Wellferon), respectively. No cytotoxicity of the interferons was observed at or near inhibitory concentrations. Ribavirin showed inhibitory activity at all three viral loads, but only at high concentrations of the drug, 0.5-5 mg/mL. At high concentrations of ribavirin (0.2-1 mg/mL) cytotoxic effects were observed on Vero E6 cells, as has been reported for other cell types (17, 18). As such, we consider ribavirin to be inactive as a sole treatment against SARS-CoV.

TABLE 3

Complete inhibition of cytopathic effect ($CIA_{100}$) at varying virus titers

| Virus load (PFU/well) | Ribavarin (μg/mL) | Wellferon (IU/mL) | Betaferon (IU/mL) | Alferon (IU/mL) | Multiferon (IU/mL) |
|---|---|---|---|---|---|
| 10,000 | 10,000 | 500,000 | 10,000 | 10,000 | 500,000 |
| 1,000 | 10,000 | 5,000 | 1,000 | 1,000 | 50 |
| 100 | 1,000 | 500 | 10 | 100 | 5 |

Figure 1:
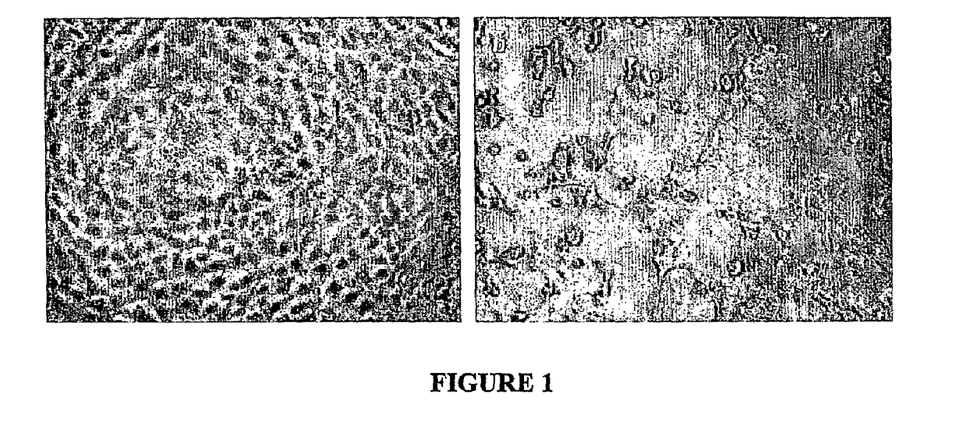
FIG. 1 is a photograph of VeroE6 cells either (a) uninfected or (b) infected SARS-CoV, demonstrating the cytopathic effects of SARS-CoV.
Figure 2:
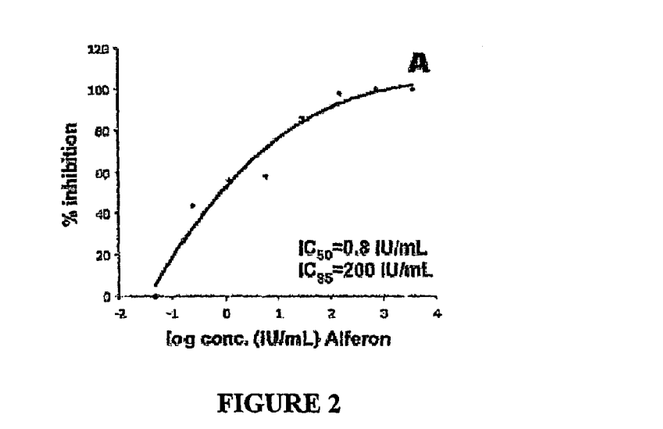
FIG. 2 is a line graph illustrating a dose response curve for interferon α-n3 as determined by a plaque reduction assay.
Figure 3:
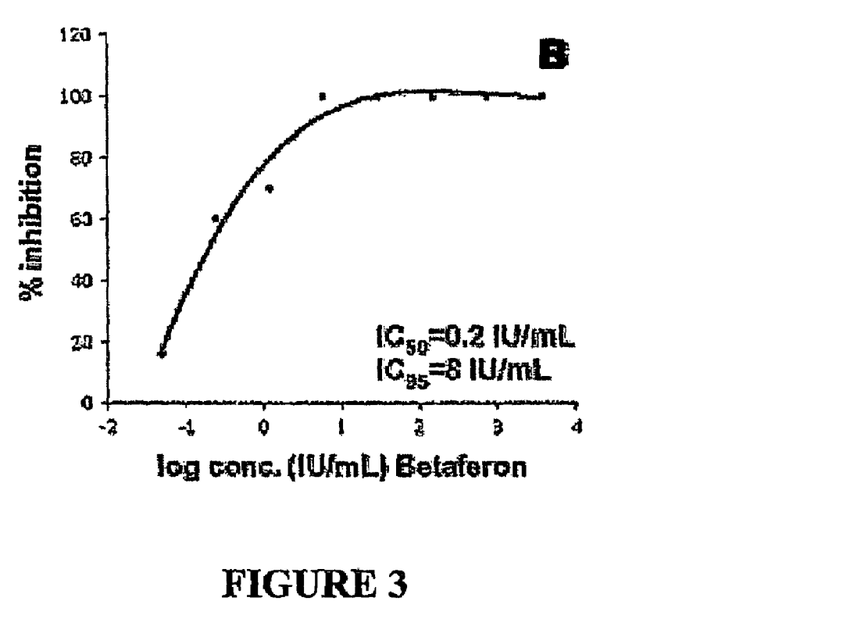
FIG. 3 is a line graph illustrating a dose response curve for interferon β-1b as determined by a plaque reduction assay.
Figure 4:
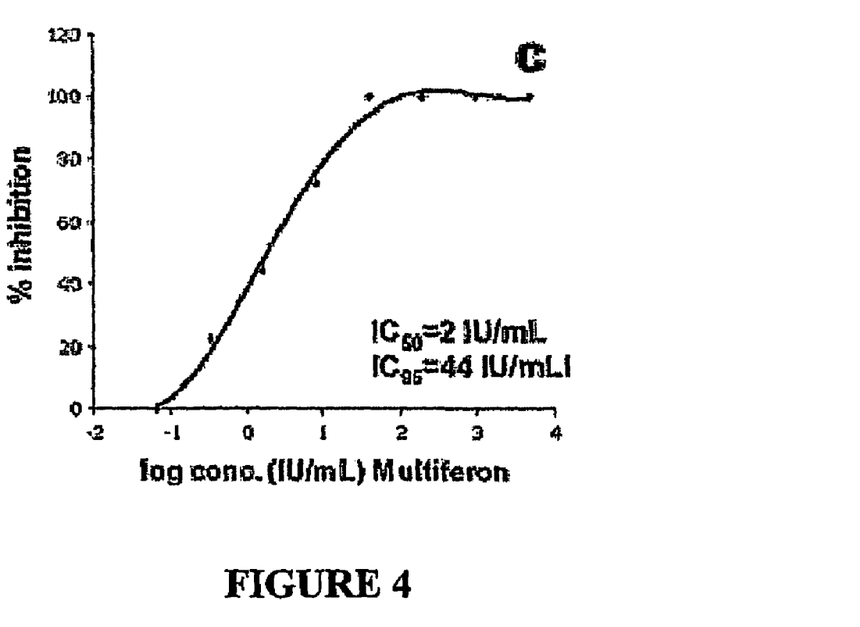
FIG. 4 is a line graph illustrating a dose response curve for human leukocyte interferon α as determined by a plaque reduction assay.

A plaque reduction assay format with 100 PFU of SARS-CoV (MOI=0.0005) was conducted to determine the $IC_{50}$ for Betaferon, Alferon, and Multiferon, the three compounds that showed greatest potency for inhibition of CPE. Additional supply was not available for testing interferon α-n1(Wellferon), as production of this drug has been discontinued. Cells were preincubated for 15 h with fivefold dilutions of drug. Viral-induced plaques, which developed in 3 days, were counted to determine the inhibitory effect of the drugs at various concentrations. All three interferon preparations displayed a dose-dependent inhibition of SARS-CoV plaque formation in this assay (FIGS. 2-4). For each of the IFNs tested, the amount required to achieve 100% inhibition of the cytopathic effect of SARS-CoV ($CIA_{100}$) varied with viral load (Table 3). The $IC_{50}$ and $IC_{95}$ were determined to be 0.2 and 8 IU/mL for Betaferon (FIG. 3), 0.8 and 200 IU/mL for Alferon (FIG. 2), and 2 and 44 IU/mL for Multiferon (FIG. 4), respectively.

As can be understood by one skilled in the art, many modifications to the exemplary embodiments described herein are possible. The invention, rather, is intended to encompass all such modification within its scope, as defined by the claims.

REFERENCES

1. World Health Organization. Acute respiratory syndrome in China—update 3: disease outbreak reported: Geneva: The Organization; 2003.
2. Lee N, Hui D H, Wu A, Chan P, Cameron P, Joynt G M, et al. A major outbreak of severe acute respiratory syndrome in Hong Kong. *N Engl J Med* 2003, 348: 1986-94.
3. Ksiazek T O, Erdman D, Goldsmith C, Zaki S R, Peret T, Emery S. et al. A novel coronavirus associated with severe acute respiratory syndrome. *N Engl J Med* 2003, 348:1953-66.
4. Tsang K W, Ho P L, Ooi G C, Yee W K, Wang T, Chan-Yeung M, et al. A cluster of cases of severe acute respiratory syndrome in Hong Kong. *N Engl J Med* 2003, 348: 1977-85.
5. Severe acute respiratory syndrome (SARS) and coronavirus testing—United States, 2003. *Morb Mortal Wkly Rep* 2003, 52:297-302.
6. Peiris J S M, Chu C M, Cheng V C, Chan K S, Hung I F, Poon L L, et al. Clinical progression and viral load in a community outbreak of coro-navirus-associated SARS pneumonia: a prospective study. *Lancet* 2003, 361:1767-72.
7. Chan-Yeung M, Yu W C. Outbreak of severe acute respiratory syndrome in Hong Kong Special Administrative Region: case report. *BMJ* 2003, 326:850-2.
8. Nicholls J M, Poon L L, Lee K N C, Ng W F, Lai S T, Leung C Y, et al. Lung pathology of fatal severe acute respiratory syndrome. *Lancet* 2003, 361:1773-8.
9. Poutanen S M, Low D E, Henry B, Finkelstein S. Rose D, Green K, et al. Identification of severe acute respiratory syndrome in Canada *N Engl J Med* 2003, 348:1995-2005.
10. Drosten C, Gunther S, Preiser W, van der Werf S, Brodt H R, Becker S, et al. Identification of a novel coronavirus in patients with severe acute respiratory syndrome. *N Engl J Med* 2003, 348:1967-76.
11. Lapinsky S E, Hawryluck L. ICU management of severe acute respiratory syndrome. *Intensive Care Med* 2003, 29:870-5.
12. Booth C M, Matukas L M, Tomlinson G A, Rachlis A R, Rose D B, Dwosh H A, et al. Clinical features and short-term outcomes of 144 patients with SARS in the greater Toronto area *JAMA* 2003, 289:2801-9. Erratum in: *JAMA* 2003, 290:334.
13. Driscoll J S. *Antiviral drugs.* Aldershot, UK: Ashgate Publishing Ltd, 2002.
14. Ruan Y J, Wei C L, Ee A L, Vega V B, Thoreau H, Su S T, et al. Comparative full length genome sequence analysis of 14 SARS coro-navirus isolates and common mutations associated with putative origins of infection. *Lancet* 2003, 361:1779-85. Erratum in: *Lancet* 2003, 361:1832.
15. Richmond J Y, McKinney R W. *Biosafety in microbiological and bio-medical laboratories. 4th ed.* Washington: U.S. Government Printing Office, 1999.
16. Al-Jabri, A. A., Wigg, M. D., Oxford, J. S. Initial in vitro screening of drug candidates for their potential antiviral activities. In: Mahy, B. W. J. and Kangro H. O. eds. *Virology Methods Manual.* Academic Press Ltd. London. 1996: 293-356.
17. Huffman, J. H., R W. Sidwell. G. P. Khare, et al. In vitro effect of 1-beta-D-ribofuranosyl-1,2,4-triazole-3-carboxamide (Virazole, ICN-1229) on deoxy-ribonucleic acid and ribonucleic acid viruses. *Antimicrob Agents Chemo.* 1973, 3:235-241.
18. Saganuma, T. and N. Ishida An evaluation of a new antiviral agent 'Virazole' against influenza virus infections. Tohoku *J. Exp. Med.* 1973, 110: 405-406.
19. Morrey J D, Smee D F, Sidwell R W, Tseng C. Identification of active antiviral compounds against a New York isolate of West Nile virus. *Antiviral Res* 2002, 55:107-16.
20. Davis G L et al. Interferon alpha2b alone or in combination with Ribavirin for the treatment of relapse of chronic hepatitis. *N. Engl. J. Med.* 1998, 339:1493-1499.
21. Poynard T P et al. Randomised trial for interferon alpha2b plus Ribavirin. *Lancet* 1998, 352;1426-1432.
22. McHutchison J G et al. Interferon alpha2b alone or in combination with Ribavirin as initial treatment for hepatitis C. *N. Engl. J Med* 1998, 339:1485-1492.

23. Pfeffer L M et al. Biological properties of recombinant alpha-interferons: 40th anniversary of the discovery of interferons. *Cancer Res.* 1998, 58:2489-2499.

24. Lee C K, Bluyssen H A and Levy D E. Regulation of interferon alpha responsiveness by the duration of Janus kinase activity *J. Biol. Chem.* 1997, 272:21872-21877.

What is claimed is:

1. A method of inhibiting SARS-coronavirus infection, comprising administering an interferon to an in vitro cell capable of being infected with SARS-CoV, wherein the interferon is IFN α-n1, IFN α-n3, human leukocyte IFN α or IFN β-1b.

2. The method of claim 1 wherein the interferon is recombinant.

3. The method of claim 2 wherein the interferon is recombinantly produced in *E. coli*.

4. The method of claim 2 wherein the interferon is recombinantly produced in mammalian cells.

5. The method of claim 1 wherein the cell is a VERO E6 cell, a peripheral blood leukocyte or a THP-1 monocyte.

6. The method of claim 1 further comprising administering to the cell an additional antiviral agent in combination with the interferon.

7. The method of claim 6 wherein the additional antiviral agent is ribavirin.

8. A method of inhibiting SARS-coronavirus infection, comprising administering a combination of recombinant interferon and ribavirin to an in vitro VERO E6 cell, a peripheral blood leukocyte or a THP-1 monocyte, said VERO E6 cell, said peripheral blood leukocyte or said THP-1 monocyte capable of being infected with SARS-CoV, wherein the interferon is IFN α-n1, IFN α-n3, human leukocyte IFN α or IFN β-1b.

* * * * *